United States Patent [19]

Berg et al.

[11] 4,100,179

[45] Jul. 11, 1978

[54] PREPARATION OF CITRACONIC ANHYDRIDE

[75] Inventors: Rudolph G. Berg, Groton; Donald S. Hetzel, New London, both of Conn.

[73] Assignee: Pfizer Inc., New York, N.Y.

[21] Appl. No.: 757,626

[22] Filed: Jan. 7, 1977

Related U.S. Application Data

[63] Continuation of Ser. No. 482,486, Jun. 24, 1974, abandoned.

[51] Int. Cl.² ............................................ C07D 307/60
[52] U.S. Cl. ................................................ 260/346.75
[58] Field of Search .................... 260/346.8 A, 346.75

[56] References Cited

U.S. PATENT DOCUMENTS 3,963,759   6/1976   Strojny .......................... 260/346.8 A

*Primary Examiner*—Henry R. Jiles
*Assistant Examiner*—Bernard Dentz
*Attorney, Agent, or Firm*—Connolly and Hutz

[57] ABSTRACT

The preparation of citraconic anhydride by continuous vapor phase oxidation of mesityl oxide, isomesityl oxide or mixtures thereof is disclosed.

2 Claims, No Drawings

PREPARATION OF CITRACONIC ANHYDRIDE

CROSS-REFERENCE TO RELATED APPLICATION

This application is a continuation of application Ser. No. 482,486 as filed Jun. 24, 1974 and now abandoned.

BACKGROUND OF THE INVENTION

This invention relates to a novel process for preparing citraconic anhydride. More specifically it relates to a continuous vapor phase oxidation process. Citraconic anhydride is useful as a curing agent for epoxy resins, and can be isomerized into itaconic acid, a valuable raw material for synthetic resins.

U.S. Pat. No. 3,701,805 discloses the vapor phase catalytic conversion of citric acid, isocitric acid, isocitric lactone, aconitic acid or their anhydrides to citraconic anhydride by heating the starting materials in admixture with an inert gas at about 215°–400° C.

It is also known in the art that citraconic anhydride can be prepared by the pyrolysis of citric acid.

SUMMARY OF THE INVENTION

It has now been found that citraconic anhydride can be readily prepared by a process which comprises contacting a gaseous mixture of about 0.2 to 5% by volume of mesityl oxide, isomesityl oxide or mixtures thereof and an oxygen-containing gas with a catalyst selected from the group consisting of vanadium oxides, bismuth oxides in combination with molybdenum oxides, and antimony oxides in combination with tungsten oxides or uranium oxides at a temperature of from about 300° to 500° C.

DETAILED DESCRIPTION OF THE INVENTION

The starting material in the process of the invention may be mesityl oxide, isomesityl oxide or mixtures thereof.

Mesityl oxide, the preferred starting material, is a well known commercially available compound which may be prepared by a number of methods. It may be obtained by the condensation of two moles of acetone in the presence of an alkali metal hydroxide to give diacetone alcohol which is then dehydrated by heating in the presence of small quantities of an acid to yield mesityl oxide. It may also be obtained directly by the condensation of acetone in the presence of a strong acid. Isomesityl oxide may be prepared by heating mesityl oxide at high temperatures.

In the process of the present invention a heated gaseous stream containing mesityl oxide or isomesityl oxide and an oxygen containing gas such as air is passed over or through a catalyst and citraconic anhydride is recovered from the exit stream. For best results, the reaction temperature range employed is about 300°–500° C. The preferred range is about 390°–460° C. The reactants should be contacted with the catalyst until the reaction is substantially complete. Adequate reaction time for this purpose will vary inversely with the temperature and generally ranges from 0.02 to 5 seconds. The preferred range is 0.04 to 2 seconds.

The catalyst used in this process is a vanadium oxide, a bismuth oxide in combination with a molybdenum oxide, or an antimony oxide in combination with a tungsten oxide or uranium oxide. Bismuth molybdate is a suitable form of bismuth oxide-molybdenum oxide combination. The preferred catalyst is one containing vanadium oxide and at least one oxide or hydroxide of an element selected from the group consisting of antimony, nickel, chromium, molybdenum, silver, titanium, germanium, phosphorus, boron, lithium, sodium and potassium. A particularly effective catalyst contains per one part by weight of vanadium, 0.1 to 0.9 parts of antimony, 0.05 to 0.35 parts of nickel and 0 to 0.02 parts each of chromium, silver and lithium as oxides or hydroxides. The catalysts may be used alone or mixed with or impregnated on a relatively inert carrier such as alumina, silica, zirconia or carborundum. A low-surface support material is preferred. The active catalyst concentration based on the total weight of support and catalyst material is preferably about 0.1–5% by weight. Standard methods of preparation of these catalysts, either unsupported or supported, are well known in the art and can be used.

The oxygen used in the reaction may be introduced in mixtures with other inert gases, e.g. nitrogen, carbon dioxide or steam. Air is preferred as the oxygen source.

The concentration of mesityl oxide or isomesityl oxide vapor in the gas stream may vary between 0.2 and 5 volume percent; however, the preferred concentration is between 0.4 and 2 volume percent. Mesityl oxide may be generated in situ by use of diacetone alcohol or by condensation of acetone.

It is known that dimethyl furan may be produced in such a process. However, we have found that this occurs primarily at higher mesityl oxide and isomesityl oxide concentrations, particularly above 7%.

The citraconic anhydride product in the gaseous effluent from the reactor can be recovered using a series of cold traps or a scrubber using water or other suitable absorption liquid. Actual isolation of citraconic anhydride can be accomplished by usual techniques, such as azeotropic drying followed by distillation.

Citraconic anhydride can easily be converted to the acid by simple hydrolysis in water, followed by isomerization to itaconic acid by procedures well known in the prior art. For example, as reported by Linstead and Mann, J. Chem. Soc. 1931, pp. 726–40, an aqueous 25% citraconic acid solution can be autoclaved at 160° C. for 8 hours to give about a 45% yield of itaconic acid, which can be easily recovered by evaporation and crystallization from water.

The following examples are provided for illustrative purposes and should not be interpreted as limiting the invention, the scope of which is defined by the appended claims. Yield figures in these examples are on a molar percent basis.

EXAMPLE I

A catalyst ("Catalyst A") was prepared by thoroughly mixing 27 g vanadium pentoxide, 0.1 g lithium hydroxide, 0.1 g silver oxide, 2.7 g nickelic oxide, 0.1 g chromic oxide and 3.3 g antimony trioxide and heating in a porcelain crucible until completely molten. The mixture was then allowed to cool and solidify. It was then crushed and screened to give a 20–40 mesh fraction. A microreactor was filled with this catalyst and an air-mesityl oxide mixture in a 99.2-0.8 by volume ratio was passed through the catalyst bed at a contact time of 0.9 seconds. The microreactor was heated by an air bath and the temperature of the air bath adjusted to give the optimum yield of citraconic anhydride. The procedure was then repeated at several different contact times and the amount of citraconic anhydride obtained in each case was observed. In each case, 100% of the starting material was consumed at the optimum reaction temperature and some maleic anhydride was co-produced. In no case was 2,4-dimethyl furan observed. Results are tabulated below:

| Contact Time (Sec.) | Optimum Airbath Temp. (° C) | Percent Yield | |
|---|---|---|---|
| | | Citraconic | Maleic |
| 0.9 | 355–370 | 21 | 6 |
| 0.45 | 380–405 | 25 | 6 |
| 0.25 | 385–400 | 28 | 4 |
| 0.16 | 385–410 | 31 | 3 |
| 0.08 | 400–420 | 36 | 6 |
| 0.04 | 410–440 | 41 | 5 |
| 0.03 | 410–440 | 41 | 5 |

Citraconic anhydride may also be observed in the product stream when a contact time of 5 seconds is employed.

EXAMPLE II

A series of catalysts were prepared by the procedure described in Example I. The starting substances and amounts by weight thereof used in the preparation of these catalysts are tabulated below:

| Catalyst | Composition |
|---|---|
| B | $V_2O_5$-100% |
| C | $V_2O_5$-97%, Ge metal 3% |
| $D_1$ | $V_2O_5$-94%, $MoO_3$ 6% |
| $D_2$ | $V_2O_5$-82%, $Ni_2O_3$-8%, $Sb_2O_3$-10% |
| E | $V_2O_5$-56.7%, $Ni_2O_3$-12%, $Sb_2O_3$-30%, $H_3BO_4$-0.2%, LiOH-0.3%, $Ag_2O$-0.3%, $Cr_2O_3$-0.3%, $P_2O_5$-0.2% |
| F | $V_2O_5$-56.3%, $Ni_2O_3$-7%, $TiO_2$-9%, $Sb_2O_3$-25%, $H_3BO_4$-1.0%, KOH-0.7%, $P_2O_5$-1.0% |
| G | $V_2O_5$-56.1%, $Ni_2O_3$-12%, $Sb_2O_3$-30%, $H_3BO_4$-0.5%, LiOH-0.3%, $Ag_2O$-0.3%, $P_2O_5$-0.5% |
| H | $V_2H_5$-5%, $MoO_3$-95% |

These catalysts were employed in the oxidation of mesityl oxide by the procedure described in Example I. Conditions and results are tabulated below:

| Catalyst | Contact Time (Sec.) | Optimum Air Bath Temp. (° C) | Percent Yield | |
|---|---|---|---|---|
| | | | Citraconic | Maleic |
| B | 0.16 | 380–410 | 28 | 7 |
| | 0.08 | 370–400 | 33 | 8 |
| C | 0.16 | 375–390 | 27 | 3 |
| | 0.08 | 345–360 | 34 | 4 |
| $D_1$ | 0.16 | 400–460 | 32 | 10 |
| $D_2$ | 0.16 | 430–460 | 29 | 3 |
| E | 0.16 | 390–400 | 34 | 7 |
| | 0.08 | 410–430 | 38 | 9 |
| F | 0.16 | 480–520 | 31 | 4 |
| G | 0.16 | 470–500 | 32 | 4 |
| H | 0.16 | 480–520 | 22 | 5 |

EXAMPLE III

Several non-fused, porous, vanadium-containing supported catalysts were prepared according to procedures disclosed in the literature. These catalysts are as follows:

| Catalyst | Composition | Preparative Procedure |
|---|---|---|
| I | Oxides of V,Ni,Mo,Na,P | U.S. Pat.No. 2,967,185 - Ex. I |
| J | Oxides of T,Vi,P | British Pat.No. 1,267,043 - Ex. I |
| K | Oxides of V,Mo | Japanese Pat.No. 7238425 - Ex. I |
| L | Oxides of V,Mo,P,B,Ag+NaCl | U.S. Pat.No. 3,535,346 - Ex. I |
| M | Oxides of V,P,Mo,Ti | Dutch Pat.No. 7301973 - Ex. I |

These catalysts were charged to the microreactor as described in Example I and observed for oxidative selectivity. Results are tabulated below:

| Catalyst | Contact Time (Sec.) | Optimum Airbath Temp. (° C) | Percent Yield | |
|---|---|---|---|---|
| | | | Citraconic | Maleic |
| I | 0.16 | 395–420 | 19 | 17 |
| J | 0.16 | 360–395 | 26 | 8 |
| | 0.08 | 430–450 | 20 | 6 |
| K | 0.16 | 435–455 | 26 | 9 |
| L | 0.16 | 370–400 | 12 | 11 |
| M | 0.16 | 380–420 | 19 | 18 |

In none of these cases was 2,4-dimethylfuran noted among the reaction products.

EXAMPLE IV

The procedure of Example I was repeated except the mesityl oxide feed concentration was 17% by volume. This increase resulted in the formation of 2,4-dimethylfuran. At the 17% feed concentration, no citraconic anhydride was observed. Details of these experiments, conducted at a contact time of 0.16 second, are tabulated below:

| Catalyst | Optimum Airbath Temp. (° C) | Percent Yield 2,4-dimethylfuran |
|---|---|---|
| A | 550 | 12 |
| B | 500 | 6 |
| I | 460 | 8 |
| J | 480 | 9 |
| K | 530 | 8 |
| L | 510 | 5 |
| M | 500 | 6 |

Under the above conditions, no citraconic or maleic anhydride was observed in the product.

EXAMPLE V

Using the procedure of Example I but varying the mesityl oxide feed concentration between the 0.8 and 17% resulted in a shift from dicarboxylic acid anhydrides to 2,4-dimethylfuran as illustrated with Catalyst A in the table below:

| Feed Conc. (%) | Optimum Air Bath Temp. (° C) | | Percent Yield | |
|---|---|---|---|---|
| | for Citraconic | for Furan | Citraconic | 2,4-dimethylfuran |
| 0.82 | 400–430 | — | 31 | 0 |

-continued

| Feed Conc. (%) | Optimum Air Bath Temp. (° C) for Citraconic | for Furan | Citraconic | Percent Yield 2,4-dimethylfuran |
|---|---|---|---|---|
| 3.0 | 350–415 | — | 3 | 0 |
| 7.3 | >520 | >520 | 1 | 9 |
| 12.9 | — | >550 | 0 | 12 |
| 20.6 | — | >560 | 0 | 8 |

EXAMPLE VI

The procedure of Example I was repeated except that varying amounts of water vapor were also fed to the reactor. The contact time was 0.16 second. Results are tabulated below:

| Composition of Feed (%) | | | Optimum Air Bath Temperature (° C) | Percent Yield | |
|---|---|---|---|---|---|
| Mesityl Oxide | Water Vapor | Air | | Citraconic | Maleic |
| 0.8 | 0 | 99.2 | 400–440 | 30 | 5 |
| 0.8 | 10 | 89.2 | 400–440 | 25 | 3 |
| 0.7 | 20 | 79.3 | 400–440 | 25 | 3 |
| 0.6 | 30 | 69.4 | 370–440 | 20 | 2 |

EXAMPLE VII

The procedure of Example I was repeated except that mixtures of oxygen and nitrogen in varying proportions were substituted for the air. The contact time was 0.16 second. Results are tabulated below:

| Composition of Feed (%) | | | Optimum Air Bath Temperature (° C) | Percent Yield | |
|---|---|---|---|---|---|
| Mesityl Oxide | O₂ | N₂ | | Citraconic | Maleic |
| 0.8 | 20 | 79.2 | 410–430 | 29 | 9 |
| 0.8 | 10 | 89.2 | 430–455 | 13 | 5 |
| 0.8 | 30 | 69.2 | 410–435 | 29 | 8 |
| 0.8 | 40 | 59.2 | 410–430 | 31 | 8 |

EXAMPLE VIII

A series of catalysts were prepared according to known procedures. These catalysts are as follows:

| Catalyst | Composition | Preparative Procedure |
|---|---|---|
| N | Oxides of Bi,Mo | Batist, et al., J. Catal. 5, 55 (1966) - B 50/50 cat. |
| O | Oxides of Bi,P,Mo | U.S. Pat.No. 2,904,580 - Ex. I |
| P | Oxides of Co,Bi,Mo | U.S. Pat.No. 3,624,146 - Ex. I |
| Q | Oxides of W,Sb | U.S. Pat.No. 3,670,006 - Ex. I |
| R | Oxides of Cu,P | U.S. Pat.No. 3,274,255 |
| S | Oxides of Cr,Fe,Zn | U.S. Pat.No. 3,450,788 - Ex. I |
| T | Oxides of U,Sb | Catalyst "21" supplied by the Vistron Company |

The above catalysts were then employed in the oxidation of mesityl oxide by the procedure described in Example I. The following results were obtained at a mesityl oxide feed concentration of 0.82% and a contact time of 0.16 second.

| Catalyst | Optimum Air Bath Temperature (° C) | Percent Yield | |
|---|---|---|---|
| | | Citraconic | Maleic |
| N | 370–390 | 4 | 2 |
| O | 415–450 | 8 | 3 |
| P | 430–450 | 6 | 23 |
| Q | 520–550 | 4 | 4 |
| T | 395–415 | 2 | 1 |

EXAMPLE IX

Two ml. of a mixture containing 91% mesityl oxide and 9% isomesityl oxide was charged at a rate of 8.0 $\mu$l/min. to a microreactor consisting of an empty 20 in. loop of 1/8 in. O.D. aluminum tubing heated in an air bath at 510° ± 10° C. Air was also introduced at a rate of 35 ml/min. The effluent was collected in dry ice traps, and the condensate was distilled at atmospheric pressure. The fraction boiling at 110°–130° was shown by NMR and gas chromatography analysis to be a mixture of 60% mesityl oxide, 25% isomesityl oxide, and 15% impurities, including acetone. The impure mixture containing an increased amount of isomesityl oxide, when oxidized according to the procedure of Example I gave yields of citraconic anhydride identical to that obtained in Example I.

What we claim is:

1. A process for preparing citraconic anhydride essentially free of 2,4-dimethylfuran which comprises contacting a gaseous mixture of about 0.4 to 2% by volume of mesityl oxide and air with a non-supported, fused vanadium oxide containing catalyst at a temperature of from about 390° to 460° C until substantial citraconic anhydride is produced, said catalyst containing 0.1 to 0.9 parts by weight of antimony, 0.05 to 0.35 parts by weight of nickel, 0 to 0.02 parts by weight of chromium, 0 to 0.02 parts by weight of silver and 0 to 0.02 parts by weight of lithium, said parts by weight being parts by weight of recited element per part by weight of vanadium and said antimony, nickel, chromium, silver and lithium being present in said catalyst as oxides or hydroxides.

2. A process for preparing citraconic anhydride essentially free of 2,4-dimethylfuran which comprises contacting a gaseous mixture of about 0.4 to 2% by volume of mesityl oxide and air with a non-supported, fused vanadium oxide containing catalyst at a temperature of from about 390 to 460° C until substantial citraconic anhydride is produced, said catalyst being the fused product of a mixture containing about 56 to 82% by weight of $V_2O_5$, 10 to 30% by weight of $Sb_2O_3$, 7 to 12% by weight of $Ni_2O_3$, 0 to 0.3% by weight of $Cr_2O_3$, 0 to 0.3% by weight of $Ag_2O$, 0 to 0.3% by weight of LiOH, 0 to 1.0% by weight of $H_3BO_4$, 0 to 1.0% by weight of $P_2O_5$, 0 to 9% by weight of $TiO_2$, and 0 to 0.7% by weight of KOH.

* * * * *